United States Patent [19]
Samson

[11] Patent Number: 5,454,795
[45] Date of Patent: Oct. 3, 1995

[54] KINK-FREE SPIRAL-WOUND CATHETER

[75] Inventor: Gene Samson, Milpitas, Calif.

[73] Assignee: Target Therapeutics, Inc., Fremont, Calif.

[21] Appl. No.: 266,540

[22] Filed: Jun. 27, 1994

[51] Int. Cl.⁶ .................................................. A61M 25/00
[52] U.S. Cl. .......................................... 604/282; 128/658
[58] Field of Search .................................. 604/280–283, 604/264; 128/657, 658, 4–6

[56] References Cited

U.S. PATENT DOCUMENTS

| | | |
|---|---|---|
| 2,437,542 | 3/1948 | Krippendorf . |
| 3,416,531 | 12/1968 | Edwards . |
| 3,924,632 | 12/1975 | Cook . |
| 4,425,919 | 1/1984 | Alston, Jr. et al. . |
| 4,484,586 | 11/1984 | McMickle et al. . |
| 4,516,972 | 5/1985 | Samson . |
| 4,739,768 | 4/1988 | Engelson . |
| 4,806,182 | 2/1989 | Rydell et al. . |
| 4,832,681 | 5/1989 | Lenck . |
| 5,037,404 | 8/1991 | Gold et al. . |
| 5,069,674 | 12/1991 | Fearnot et al. . |
| 5,176,660 | 1/1993 | Truckai . |
| 5,178,158 | 1/1993 | de Toledo . |
| 5,217,482 | 6/1993 | Keith . |
| 5,275,152 | 1/1994 | Krauter et al. ..................... 604/282 X |
| 5,279,596 | 1/1994 | Castaneda et al. ................ 604/280 X |
| 5,336,205 | 8/1994 | Zenzen et al. ......................... 604/280 |
| 5,357,955 | 10/1994 | Wolf et al. . |

Primary Examiner—John D. Yasko
Attorney, Agent, or Firm—Morrison & Foerster

[57] ABSTRACT

This invention is a surgical device. In particular, it is a catheter suitable for treating a tissue target within the body, which target is accessible through the vascular system. Central to the invention is the use of stiffener ribbons, typically metallic, wound within the catheter body in such a way as to create a catheter having controllable stiffness.

55 Claims, 4 Drawing Sheets

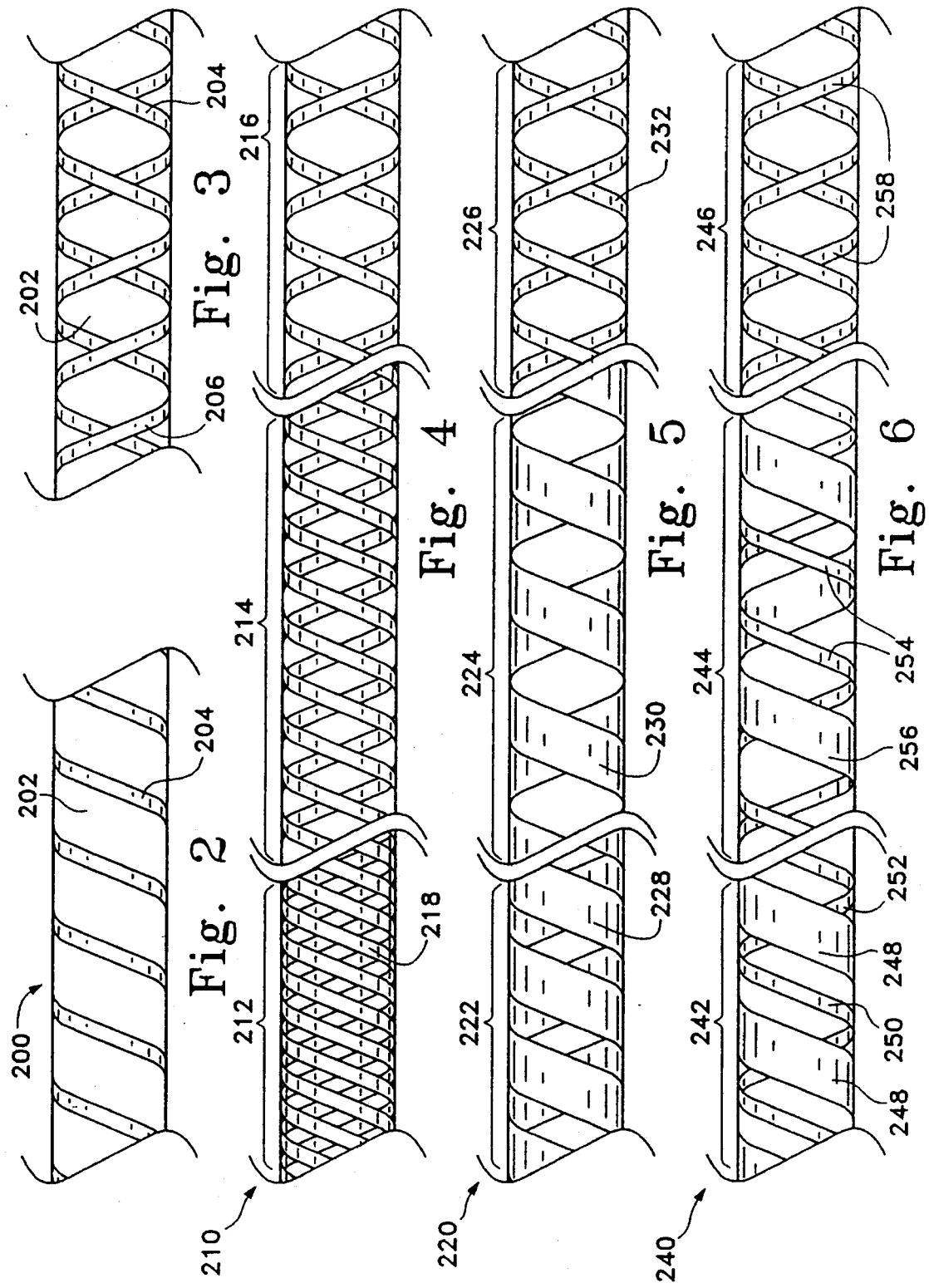

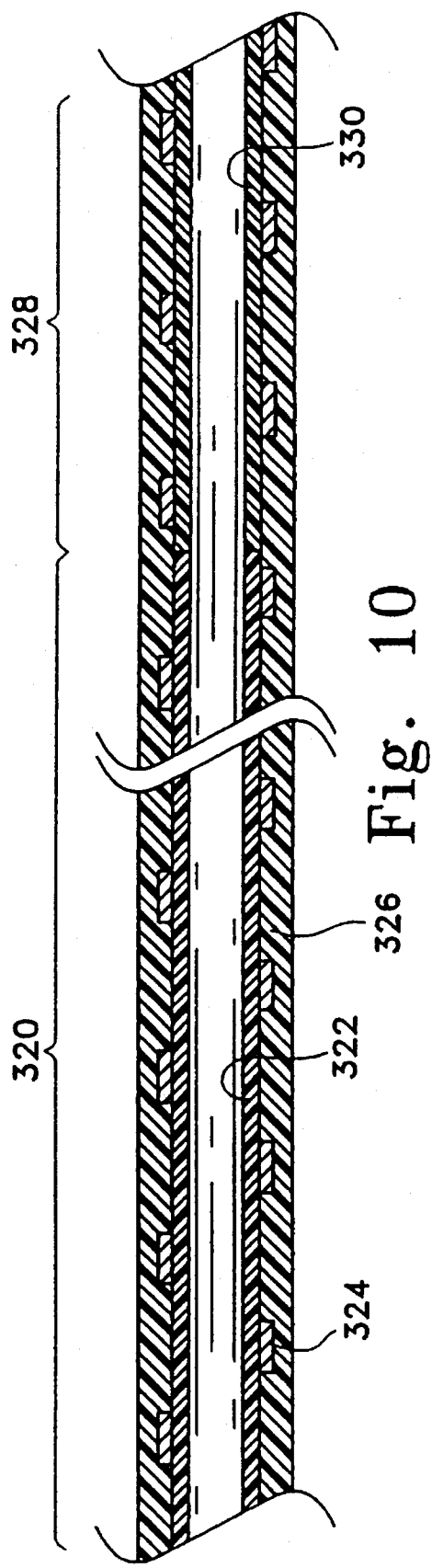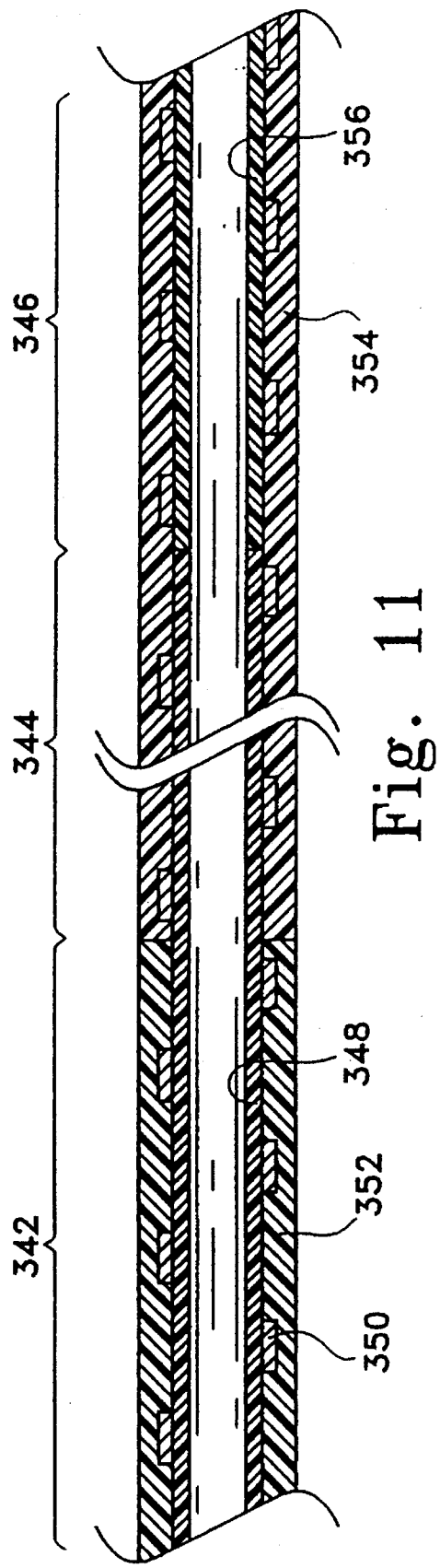

KINK-FREE SPIRAL-WOUND CATHETER

FIELD OF THE INVENTION

This invention is a surgical device. In particular, it is a catheter suitable for treating a tissue target within the body, which target is accessible through the vascular system. Central to the invention is the use of stiffener ribbons, typically metallic, wound within the catheter body in such a way as to create a catheter having controllable stiffness.

BACKGROUND OF THE INVENTION

Catheters are increasingly used to access remote regions of the human body and, in doing so, delivering diagnostic or therapeutic agents to those sites. In particular, catheters which use the circulatory system as the pathway to these treatment sites are especially useful. For instance, it is commonplace to treat diseases of the circulatory system via angioplasty (PCTA) using catheters having balloons on their distal tips. It is similarly common that those catheters are used to deliver a radiopaque agent to that site prior to the PCTA procedure to view the problem prior to treatment.

Often the target which one desires to access by catheter is within a soft tissue such as the liver or the brain. The difficulty in reaching such a site must be apparent even to the casual observer. The catheter must be introduced through a large artery such as those found in the groin or the neck and be passed through ever more narrow regions of the arterial system until the catheter reaches a selected site. Often such pathways will wind back upon themselves in a multi-looped path. These catheters are fairly difficult to design and utilize in that they must be fairly stiff at their proximal end so to allow the pushing and manipulation of the catheter as it progresses through the body, and yet must be sufficiently flexible at the distal end to allow passage of the catheter tip through the loops and increasingly smaller blood vessels mentioned above and yet at the same time not cause significant trauma to the blood vessel or to the surrounding tissue. Further details on the problems and an early, but yet effective, way of designing a catheter for such a traversal may be found in U.S. Pat. No. 4,739,768, to Engelson. These catheters are designed to be used with a guidewire. A guidewire is simply a wire, typically of very sophisticated design, which is the "scout" for the catheter. The catheter fits over and slides along the guidewire as it passes through the vasculature. Said another way, the guidewire is used to select the proper path through the vasculature with the urging of the attending physician and the catheter slides along behind once the proper path is established.

There are other ways of causing a catheter to proceed through the human vasculature to a selected site, but a guidewire-aided catheter is considered to be both quite quick and somewhat more accurate than the other procedures. One such alternative procedure is the use of a flow-directed catheter. These devices often have a small balloon situated on the distal end of the catheter which may be alternatively deflated and inflated as the need to select a route for the catheter is encountered.

This invention is an adaptable one and may be used in a variety of catheter formats. The invention utilizes the concept of combining a polymeric tubing with one or one or more spirally wound ribbons to control the stiffness of the resultant catheter body. This catheter may be used in conjunction with a guidewire, but the catheter body may also be used as a flow-directed catheter with the attachment of a balloon or in combination with a specifically flexible tip, as is seen, for instance, in U.S. application Ser. No. 08/023,805 to Zenzen et al., the entirety of which is incorporated by reference.

The use of ribbons in winding a catheter body is not a novel concept. However, none have used this concept to produce a catheter which has the physical capabilities of the catheter of this invention.

Examples of previously disclosed catheters include U.S. Pat. No. 2,437,542, to Crippendorf. Crippendorf describes a "catheter-type instrument" which is typically used as a ureteral or urethral catheter. The physical design is said to be one having a distal section of greater flexibility and a proximal section of lesser flexibility. The device is made of intertwined threads of silk, cotton, or some synthetic fiber. It is made by impregnating a fabric-based tube with a stiffening medium which renders the tube stiff yet flexible. The thus-plasticized tubing is then dipped in some other medium to allow the formation of a flexible varnish of material such as a tung oil base or a phenolic resin and a suitable plasticizer. There is no indication that this device is of the flexibility required herein. Additionally, it appears to be the type which is used in some region other than in the periphery or in soft tissues of the body.

Similarly, U.S. Pat. No. 3,416,531, to Edwards, shows a catheter having braiding-edge walls. The device further has layers of other polymers such as TEFLON and the like. The strands found in the braiding in the walls appear to be threads having classic circular cross-sections. There is no suggestion of constructing a device using ribbon materials. Furthermore, the device is shown to be fairly stiff in that it is designed so that it may be bent using a fairly large handle at its proximal end. There is no suggestion to either merely wind ribbon onto a polymeric substrate to form a catheter or, in particular, to make one of such flexibility as is required herein.

U.S. Pat. No. 4,484,586 shows a method for the production of a hollow, conductive medical tubing. The conductive wires are placed in the walls of hollow tubing specifically for implantation in the human body, particularly for pacemaker leads. The tubing is made of, preferably, an annealed copper wire which has been coated with a body-compatible polymer such as a polyurethane or a silicone. The copper wire is coated and then used in a device which winds the wire into a tube. The wound substrate is then coated with another polymer to produce a tubing having spiral conducting wires in its wall.

A document showing the use of a helically wound ribbon of flexible material in a catheter is U.S. Pat. No. 4,516,972, to Samson. This device is a guiding catheter and it may be produced from one or more wound ribbons. The preferred ribbon is an aramid material known as Kevlar 49. Again, this device is a device which must be fairly stiff. It is a device which is designed to take a "set" and remain in a particular configuration as another catheter is passed through it. It must be soft enough so as not to cause substantial trauma, but it is certainly not for use as a guidewire. It would not meet the flexibility criteria required of the inventive catheter described herein.

U.S. Pat. No. 4,806,182, to Rydell et al., shows a device using stainless steel braid imbedded in its wall and an inner layer of polyfluorocarbon. The process also described therein is a way to laminate the polyfluorocarbon to a polyurethane inner liner so as prevent delamination.

U.S. Pat. No. 4,832,681, to Lenck, shows a method and apparatus for artificial fertilization. The device itself is a long portion of tubing which, depending upon its specific materials of construction, may be made somewhat stiffer by the addition of spiral reinforcement comprising stainless steel wire.

Another catheter showing the use of braided wire is shown in U.S. Pat. No. 5,037,404, to Gold et al. Mention is made in Gold et al of the concept of varying the pitch angle between wound strands so to result in a device having differing flexibilities at differing portions of the device. The differing flexibilities are caused by the difference in pitch angle. No mention is made of the use of ribbon, nor is any specific mention made of the particular uses to which the Gold et al. device may be placed.

U.S. Pat. No. 5,069,674 shows a small diameter epidural catheter which is flexible and kink-resistant when flexed. The wall has a composite structure including a helical coil, typically stainless steel or the like, a tubular sheath typically of a polymer, and a safety wire which is spiraled about the coil and is often in the shape of a ribbon.

U.S. Pat. No. 5,176,660 shows the production of catheters having reinforcing strands in their sheath wall. The metallic strands are wound throughout the tubular sheath in a helical crossing pattern so to produce a substantially stronger sheath. The reinforcing filaments are used to increase the longitudinal stiffness of the catheter for good "pushability". The device appears to be quite strong and is wound at a tension of about 250,000 lb./in.$^2$ or more. The flat strands themselves are said to have a width of between 0.006 and 0.020 inches and a thickness of 0.0015 and 0.004 inches. There is no suggestion to use these concepts in devices having the flexibility and other configurations described below.

U.S. Pat. No. 5,178,158, to de Toledo, shows a device which is a convertible wire having use either as a guidewire or as a catheter. The coil appears to be a ribbon which forms an internal passage through the coil/catheter device. No interior coating is applied.

U.S. Pat. No. 5,217,482 shows a balloon catheter having a stainless steel hypotube catheter shaft and a distal balloon. Certain sections of the device shown in the patent use a spiral ribbon of stainless steel secured to the outer sleeve by a suitable adhesive to act as a transition section from a section of very high stiffness to a section of comparatively low stiffness.

None of these devices are catheters which have the critical bend diameter required herein, nor do they have the compression strength, or flexibility of the present invention.

SUMMARY OF THE INVENTION

This invention is a catheter section made up, desirably, of an inner tubing liner, one or more spirally wound stiffener ribbons, and an outer covering. The inner tubing liner, when used, typically is a polymeric section of tubing which may be a thermoplastic and is miscible upon heating with the material found in the outer covering. The inner layer may be a thermosetting material which adheres to the outer material or which may be adhesively bound to the outer material. In any event, the two or more polymeric layers are to hold the spirally wound stiffener ribbons in place in the catheter assembly.

The stiffener ribbon may be wound onto the inner tubing liner in a number of different ways. It may be, in its most basic form, a single strand of ribbon wound in a single direction. It may a number of ribbons of differing sizes and compositions wound each way around the tubing liner. The ribbons are typically metallic but may be of other materials.

The various catheter sections may be formed into an integral catheter assembly. Wise choices of materials permit the catheter to be of a smaller overall diameter with a superior critical diameter. The catheter may be designed to integrate lubricious materials into the base design of a particular catheter product without adding extraneous thickness and stiffness. The catheter may be wholly constructed of materials which are stable to radioactive sterilization procedures.

BRIEF DESCRIPTION OF THE DRAWINGS

FIG. 2 shows, in magnification, a section of the inner portion of one inventive section of this catheter.

FIG. 3 shows, in magnification, a section of the inner portion of this catheter.

FIGS. 4, 5, and 6 show fragmentary, cross sectional views of various configurations of the inner sections of multi-section catheters made according to this invention.

FIGS. 10 and 11 show highly desirable embodiments, in fractional cross-section, of multisection catheters made according to this invention.

DESCRIPTION OF THE INVENTION

This invention is a kink-resistant catheter section or catheter. It is a composite device having at least one section including a helically wound ribbon stiffener coaxially incorporated into that section or sections. The catheter is configured so that at least the distal portion of the catheter has a critical bend diameter of no more than 3.5 mm, preferably no more than 2.5 mm, and most preferably no more than 1.5 mm. Additionally, that section desirably has a lateral stiffness, such as would be measured by a Tinius-Olsen Stiffness Tester, of at least 6,500° of deflection/inch-pound (measured at 20°–30° of deflection, 0.005 lb, over a 0.25" span), preferably 7,500° of deflection/inch-pound, and most preferably 9,500° of deflection/inch-pound. We have additionally found that the radial compression strength of the section is quite high as compared to other distal sections found on comparable catheter distal sections.

Figure 1:
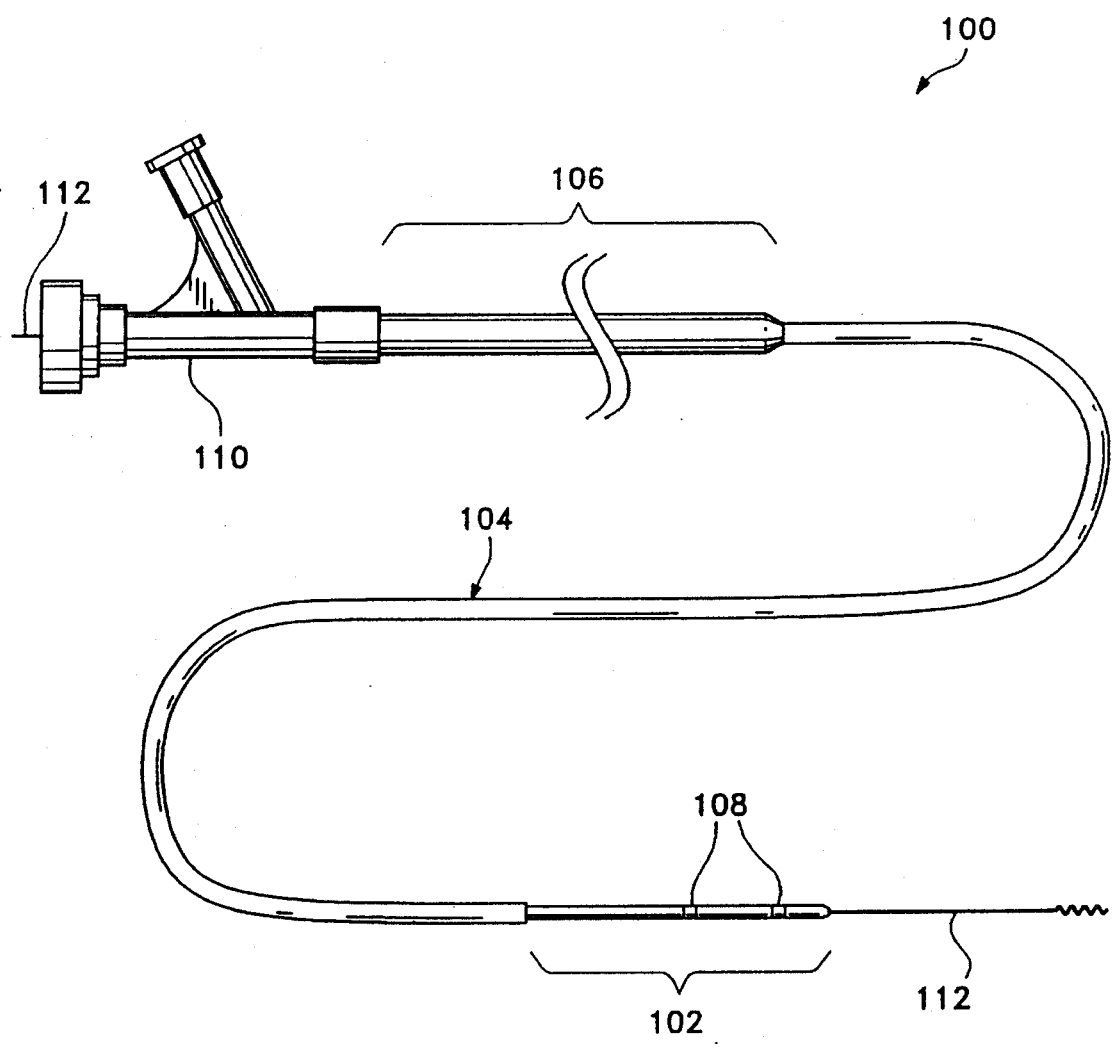
FIG. 1 shows, in side view, a typical three section catheter.

A typical multi-section catheter (100) which may incorporate the concepts of this invention is shown in FIG. 1. Such a catheter is described in more detail in U.S. Pat. No. 4,739,768, to Engelson, (the entirety of which is incorporated by reference) and is suitable for neurological and peripheral vascular applications. Clearly, then, it is also suitable for less demanding service such as might be encountered in access and treatment of the heart. One difficulty which has arisen as higher demands for length have been placed on these catheters is that the diameter of the distal section necessarily becomes smaller and smaller. This is so since the longer catheters must reach ever more smaller vascular areas. This smaller diameter requires a concomitant thinning of the wall section. The thinner section walls may kink or ripple when actively pushed along the guidewire or when vasoocclusive devices are pushed through the catheter's lumen. The typical configuration shown in FIG. 1 has a distal section (102) having significant flexibility, an intermediate section (104) which is typically less flexible, and a long proximal section (106) which in turn is least flexible. The distal section (102) is flexible and soft to allow deep penetration of the extraordinary convolutions of the neurological vasculature without trauma. Various known and necessary accessories to the catheter assembly, e.g., one or more radiopaque bands (108) at the distal region to allow viewing of the position of the distal region under fluoroscopy and a luer assembly (110) for guidewire (112) and fluids access, are also shown in FIG. 1. The typical dimensions of this catheter are:

| | |
|---|---|
| Overall length: | 60–200 cm |
| Proximal Section (106): | 60–150 cm |
| Intermediate Section (104): | 20–50 cm |
| Distal Section (102): | 2.5–30 cm |

Obviously, these dimensions are not particularly critical to this invention and are selected as a function of the malady treated and its site within the body. However, as will be discussed below, use of the spiral wound ribbon permits the walls of the catheter to be somewhat thinner with no diminution of performance, e.g., crush strength or flexibility, or indeed, an improvement in performance.

FIG. 2 shows a magnified section of a catheter body or section (200) showing the most basic aspects of one variation of the invention. As shown there, the catheter body or section has an inner tubing member (202) and a helically wound ribbon (204). The inner tubing member (202) may, depending on the section of the catheter, be of any of a variety of polymers, variously stiff or flexible. For instance, if the section (200) is used as a proximal section, the inner tubing (202) may be a polyimide, polymides such as the Nylons, high density polyethylene (HDPE), polypropylene, polyvinylchloride, various fluoropolymers (for instance: PTFE, FEP, vinylidene fluoride, mixtures, alloys, copolymers, block copolymers, etc.), polysulfones or the like. Blends, alloys, mixtures, copolymers, block copolymers, of these materials are also suitable, if desired.

If a more flexible section is required, the inner tubing member (202) may be a polyurethane, low density polyethylene (LDPE), polyvinylchloride, THV, etc. and other polymers of suitable softness or modulus of elasticity.

We have also found that this catheter design allows us to use in the distal portion of the catheter, thin-walled tubing of inherently more slippery polymers, such as PTFE and FEP and their mixtures, which have the benefit of being lubricious but otherwise would have been used in a somewhat greater thickness. Clearly, greater thickness tubing of these polymers results in the tubing being somewhat stiffer. The wall thickness of the inner tubing liner (202) may be as thin as 0.5 mil and as thick as 10 mil, depending upon catheter usage, portion of the catheter chosen, polymer choice, and the style of catheter. Typical choices for inner tubing liner polymers would be:

| Catheter Section | Example Polymer | Wall Thickness (mil) |
|---|---|---|
| Distal | Polyethylenes | 0.5–3 |
| | Fluoropolymers | 0.5–3 |
| | Polyurethane | 0.5–3 |

-continued

| Catheter Section | Example Polymer | Wall Thickness (mil) |
|---|---|---|
| Intermediate | Polyethylenes | 1–4 |
| | Fluoropolymers | 1–4 |
| | polyolefin blends | 1–4 |
| | Polypropylene | 1–4 |
| Proximal | LDPE/HDPE | 1–4 |
| | Polypropylene | 1–4 |
| | Fluoropolymers | 1–4 |
| | Polyimide | 1–4 |

These dimensions are obviously only ranges and each catheter variation must be carefully designed for the specific purpose to which it is placed.

Preferred combinations of polymers for catheter configurations will also be discussed below. It should also be noted at this point that each of the polymers discussed herein may be used in conjunction with radiopaque material such as barium sulfate, bismuth trioxide, bismuth carbonate, powdered tungsten, powdered tantalum, or the like so that the location of the various pieces of tubing may be radiographically visualized within the vessel.

The spiral wound ribbon (204) shown in FIG. 2 may also be of a variety of different materials. Although metallic ribbons are preferred because of their strength-to-weight ratios, fibrous materials (both synthetic and natural) may also be used. Preferred, because of cost, strength, and ready availability are stainless steels (308, 304, 318, etc.) and tungsten alloys. Also acceptable, but with a penalty variously in strength, density, and ductility, are precious metals such as gold, platinum, palladium, rhodium and the like, as well as alloys of these metals. Alloys of many of these precious metals with, for instance, tungsten, have lower ductility than the neat precious metal.

The class of alloys known as super-elastic alloys is also a desirable selection, although the processability of these alloys into small ribbons is not routine. Preferred superelastic alloys include the class of materials known as nitinol—alloys discovered by the U.S. Navy Ordnance Laboratory. These materials are discussed at length in U.S. Pat. Nos. 3,174,851 to Buehler et al., 3,351,463 to Rozner et al., and 3,753,700 to Harrison et al. These alloys are not readily commercially available in the small ribbons required by the invention described here, but for very high performance catheters are excellent choices.

Metallic ribbons (204) that are suitable for use in this invention are desirably between 0.75 mil and 1.5 mil in thickness and 2.5 mil and 8.0 mil in width. For superelastic alloys, particularly nitinol, the thickness and width may be somewhat finer, e.g., down to 0.5 mil. and 1.0 mil., respectively. Currently preferred, based on strength, cost and availability are stainless steel ribbons of 1 mil.×3 mil., 2 mil.×6 mil., and 2 mil.×8 mil.

Suitable non-metallic ribbons include those made of polyaramids (e.g., KEVLAR), carbon fibers, and lower performance polymers such as Dacron and the Nylons. Acceptable natural fibers include silk and cotton. It should be observed that the preferred manner of using non-metallic ribbons in this invention is in combination with metallic ribbons to allow "tuning" of the stiffness of the resulting composite or as an opposite "handed" ribbon in the composite to lessen the tendency of the metallic ribbon to unwind and hence create bumps or constrictions in the catheter lumen.

Returning to FIG. 2, the stiffener ribbon (204) may be simply wound onto the inner tubing liner (202). Depending upon the choice of materials for inner tubing liner (202), the stiffener ribbon (204) may be applied with an adhesive. The adhesive is used primarily to cause the outer cover (discussed below) to adhere to the inner tubing liner (202). We prefer to choose polymers for the components of the catheter which inherently adhere to each other, e.g., certain polyethylenes and polyimides, or thermoplastics, which are miscible with each other upon appropriate heating, e.g., PEBAX and polyurethanes. When we construct a catheter section using only the materials found in the respective tubing sections, or using a third material to improve the miscibility of the materials found in the respective liners and cover, we refer to that construction as being "binderless." If an adhesive is used to promote the adherence and outer layer to an inner layer, that would not be "binderless."

Thermoplastics which are inherently adherent to each other or are miscible with each other are preferred in the intermediate and distal areas of the catheter since the noted adhesives may then be omitted and the various stiffener ribbons held in place by the junction of the inner tubing liner (202) and the outer cover (not shown in this Figure).

The wound inner sector shown in FIG. 2 incorporates a helically wound stiffener ribbon (204) wound in one direction or "hand". FIG. 3 shows a second stiffener ribbon (206) wound in a second direction or "handedness" around both the first stiffener ribbon (204) and the inner tubing liner (202).

For economies of production, it is desirable to "gang-wind" the ribbon stiffeners onto the inner tubing liner. That is to say, for instance, that a catheter having a primary or first stiffener ribbon (204) with a spacing of twelve turns per inch can be produced by turning the catheter tubing twelve times and wrapping a single ribbon about it or by turning the catheter tubing six times and wrapping a pair of stiffener ribbons spaced apart so to produce a device appearing to have twelve turns of ribbon thereon. Similarly, the inner tubing can be turned four times with a gang-wind of three ribbons, etc. As will be discussed below, none of the wound ribbons of necessity must be of a consistent size. Each stiffener ribbon on each section of the catheter assembly may be of a different width and thickness.

A further aspect of this invention is shown in FIG. 4. The catheter (210) has three discrete sections: a proximal section (212), an intermediate section (214) and a distal section (216). This catheter (210) is analogous in overall function to that shown in FIG. 1. In particular, the proximal section (212) of the catheter is stiffest in that the number of stiffener ribbons (218) are wound onto the tubular substrate is densest. The distal portion (216) is wound to the other extreme in that the number of stiffener ribbons (218) is least dense. The intermediate section (214) is wound with stiffener ribbons to a density intermediate between the two adjacent sections. As has been noted elsewhere, although the majority of instances noted herein discuss three-section catheters, the invention is not so limited. The inventive catheters may have fewer or may have more sections depending upon the ultimate use to which the catheter is placed.

The FIG. 4 catheter sections are shown using stiffener ribbons in each section of the same size. The various stiffener ribbons are of the same size in each direction of wind as well. The density of turns is one way in which to control the overall stiffness of the catheter section.

Another method for controlling stiffness is shown in FIG. 5. As was the case with the catheter shown in FIG. 4, a three piece catheter (220) is shown. In this instance, however, the manner of controlling the stiffness is different. In this embodiment, the width of the respective stiffener ribbons is varied to acquire the specific desired stiffness. For instance, in catheter assembly (220), the proximal portion (222) uses comparatively wide stiffener ribbons (228) shown wound in both directions. Intermediate section (224) utilizes narrower stiffener ribbons (230) and distal section (226) uses the narrowest stiffener ribbons (232).

Although, again, each section is portrayed as having ribbons of equal size, wound in each direction, such is obviously not a requirement of the invention.

The width of the ribbons may be chosen in such a way that different sizes are wound in different directions or multiple sizes of stiffener ribbon may be gang-wound in the same direction or, obviously, a combination of these themes are also appropriate.

FIG. 6 shows a three-part catheter to (240) also having an exemplative three-part construction: proximal section (242), intermediate section (244) and distal section (246). In this configuration, the proximal section (242) utilizes both wide stiffener ribbons (248) and narrow stiffener ribbons (250) in one wind direction and only narrow stiffener ribbons (252) in the other wind direction. The intermediate sector (244) uses the same collection of ribbons in each wind direction: specifically, two narrow ribbons (254) and a single wide ribbon (256). The distal section (246) utilizes but a single width of ribbon (258) in each wind direction. This drawing depicts the wide variation in "tuning," the stiffness of the catheter sections for particular purposes by use Of varied spacing of the stiffener ribbon winding, the use of various width ribbons, as well as the use of combinations of ribbon width.

Once the stiffener ribbon is wound onto the inner tubing liner, an outer covering must then be applied.

Figure 7:
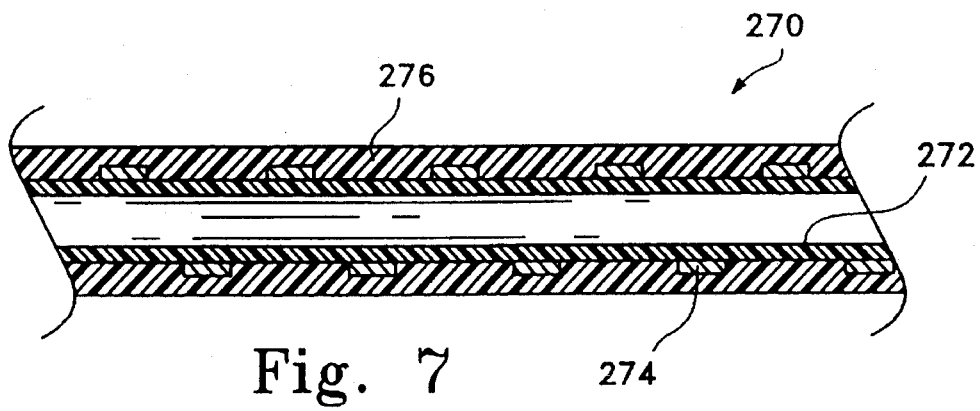
FIG. 7 shows, in cross-section, a typical catheter section made according to this invention.

FIG. 7 shows, in cross-section, a section of (270) of catheter having an inner tubing liner (272), a stiffener ribbon (274), and an outer cover (276). The outer cover or layer may be applied in a variety of ways. As noted above, the preferred way is to shrink an appropriate tubing onto the stiffener ribbon and continue to shrink the tubing in such a way that it fills the interstices between windings of the stiffener ribbon (274) as is shown in FIG. 7. This allows the outer covering (276) directly to contact the inner tubing liner (272). Even more desirably, the outer tubing (276) should be further heated to allow mixing of the outer covering (276) with the inner tubing liner (272) at their interface so as to form a strong integral catheter section (270). If the two polymer layers are mixed at this interface, so much the better for the strength of the bond.

It should be apparent that the outer layer (276) may also be applied by dipping the inner tubing layer (272)/stiffener ribbon (274) into a molten polymer bath or into a polymer dissolved in a solid or into a suspension or latex comprising the outer cover polymer. Obviously, the cover may be placed on the catheter by spraying or otherwise applying the material. Included in such a class are the polyurethanes, polysilicones, polyvinylpyrrolidone, etc.

The catheter and catheter sections of this invention may be coated or otherwise treated to increase their lubricity.

Figure 8:
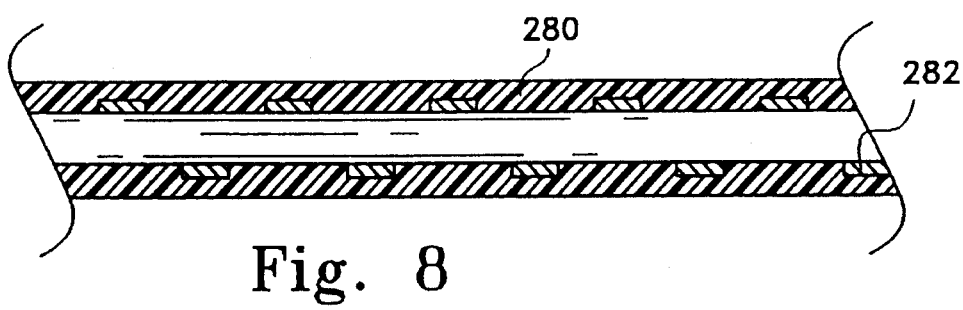
FIG. 8 shows a fragmentary cross-sectional view of a catheter section made according to this invention.

FIG. 8 shows another variation of the inventive catheter body in which the inner polymeric layer is eliminated. The section is quite simple in construction. Specifically, an outer layer of a polymeric material (280) is placed over a previously wound coil (282). These outer layers may preferably be made of a heat shrinkable tubing having a thin wall thickness. Polyethylenes, polyurethanes, polyvinylchloride, polyfluoroethylenes, and blends or copolymers containing such polymers (e.g., THV) are especially preferred.

The FIG. 8 variation, when used with a coil (282) wire or ribbon having a pitch selected to provide spacing between adjacent turns of the coil, is especially useful as a distal or midsection of a catheter in that it is quite flexible, retains kink resistance, and is quite easy to construct.

As was noted above, the most distal portion of the distal section of this catheter (and preferably other sections as well) have a critical bend diameter of no more than 3.5 mm, preferably no more than 2.5 mm, and most preferably no more than 1.5 mm. Additionally, that section desirably has a lateral stiffness, such as would be measured by a Tinius-Olsen Stiffness Tester, of at least 6,500° of deflection/inch-pound (measured at 20°–30° of deflection, 0.005 lb, over a 0.25" span), preferably 7,500° of deflection/inch-pound, and most preferably 9,500° of deflection/inch-pound.

Figure 9A:
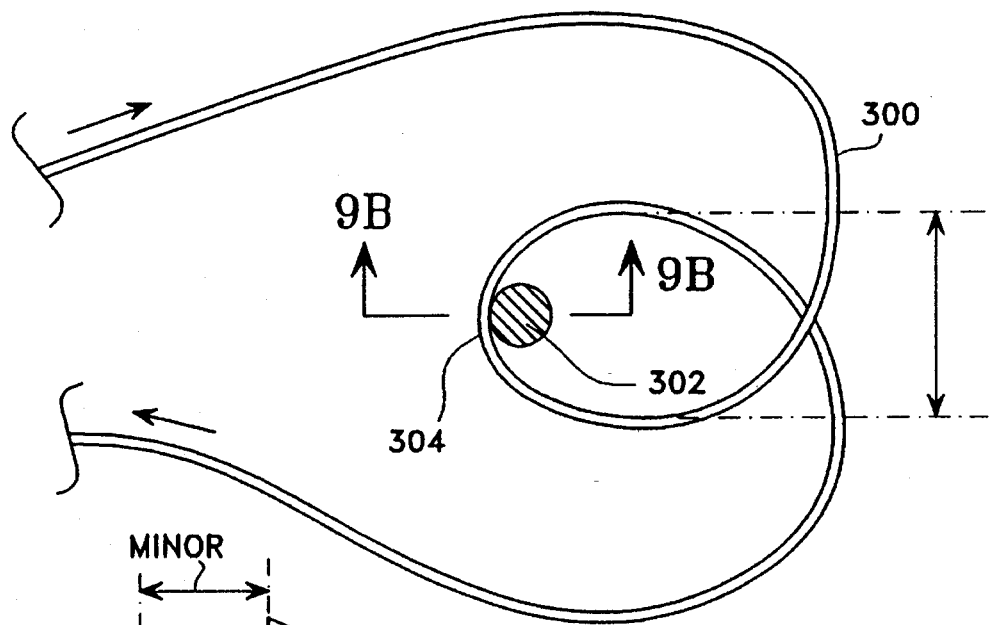
FIGS. 9A and 9B show details of the method of testing the "critical bend diameter" of this invention.
Figure 9B:
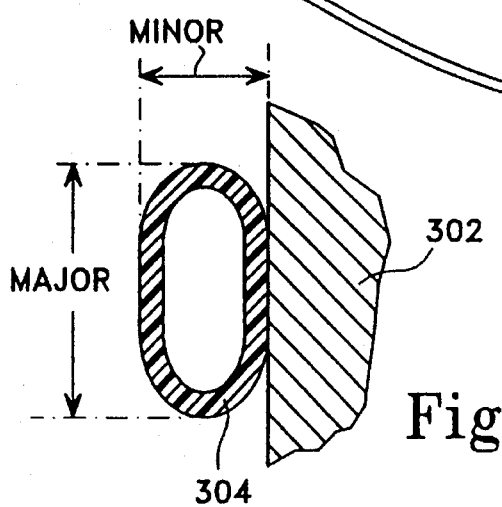

The test we utilize for critical bend diameter determination uses a test shown schematically in FIGS. 9A and 9B.

In general, as shown in FIG. 9A, a catheter section (300) is placed between two plates (desirably of plastic or glass or the like for visibility) and often with an optional peg (302) to hold the catheter section (300) loop in place. The ends of the catheter are then pulled until a kink appears in the body of the catheter. Alternatively, the ratio of the outer diameters (major diameter:minor diameter) as measured at apex (304) reaches a value of 1.5. FIG. 9B shows the cross section of the catheter sector at (304) and further shows the manner in which the major diameter and the minor diameter are measured. These two methods provide comparable results although the latter method is more repeatable.

Many times herein, we refer to the "region" section of the catheter. Where the context permits, by "region" we mean within 15% of the point specified. For instance, "the distal region of the distal section" would refer to the most distal 15% in length of the distal section.

Two highly desirable catheter designs are shown in FIGS. 10 and 11, in fragmentary cross-section. In particular, FIG. 10 shows a catheter having two sections of different stiffness. The proximal section (320) is made up of an inner tubing liner (322) of polyimide, a spiral wound stiffener ribbon (324) of 1 mil.×3 mil. stainless steel, and an outer covering (326) of shrink wrap FEP-vinylidene fluoride (THV-200). The distal section (328) shares the same outer covering (326) but also has an inner tubing liner (330) of FEP-vinylidene fluoride (THV-200). It may be observed that the spacing between the winds of stiffener ribbon (326) is quite different in the two sections. The proximal section has a twelve turn per inch spacing but the distal section has a wind spacing of only four turns per inch.

FIG. 11 shows a three flexibility sector catheter (340) with a proximal section (342), an intermediate section (344), and a distal section (346). The proximal section is made up of an inner liner (348) of FEP; a spiral-wound 1×3 millimeter stainless steel ribbon (350) of twelve turns per inch spacing is turned each way on the inner liner; and an outer layer of FEP-vinylidene fluoride (THV-500).

The intermediate section (344) includes an extension of the proximal inner liner (348) found in the proximal section (342) and an outer distal section (354). The outer distal covering (354) may also be of FEP (but of a somewhat softer makeup than the proximal inner liner (348)) but preferably is of a FEP-vinylidene fluoride such as THV-200. The FEP and FEP-vinylidene copolymer are miscible when heated. The wind-spacing in this section has been spread out to a spacing of nine turns per inch.

Finally, the distal section (346) is made up of an extension of the outer distal section (354) and an inner distal tubing (356). In this case, the inner distal section is of the same material as that of the outer distal section (356). The wind-spacing in this section has been spread out to a spacing of six turns per inch.

This invention has been described and specific examples of the invention have portrayed. The use of those specifics is not intended to limit the invention in any way. Additionally, to the extent that there are variations of the invention which are within the spirit of the disclosure and yet are equivalent to the inventions found in the claims, it is our intent that this patent cover those variations as well.

I claim as my invention:

1. A catheter section comprising:

an elongate tubular member having a proximal end and a distal end and a passageway defining an inner lumen extending between those ends, said elongate tubular member comprising an inner tubular liner of a first liner material in coaxial relationship with an outer tubular cover comprising a first cover material, and at least a first ribbon stiffener having a handedness and spirally and coaxially wound exterior to said inner tubular liner and covered by said outer tubular cover, and the catheter section, in the region of the distal end, has a critical bend diameter of no more than 3.5 mm and a lateral flexibility of greater than 6500°/in-lb.

2. The catheter section of claim 1 wherein the section has a lateral flexibility of greater than 8500°/in-lb.

3. The catheter section of claim 1 wherein the where the liner material and cover material are miscible in melt form.

4. The catheter section of claim 3 where the liner material is admixed with the cover material in the coaxial region of the first ribbon stiffener.

5. The catheter section of claim 1 which is binderless between the inner tubular liner and the outer tubular cover.

6. The catheter section of claim 1 where the liner material and cover material are radiation sterilizable without substantial degradation of their physical attributes.

7. The catheter section of claim 1 where the first ribbon stiffener spirally and coaxially wound upon said inner tubular liner where the catheter section additionally comprises a second ribbon stiffener of opposite handedness to the first ribbon stiffener spirally and coaxially wound upon said first ribbon stiffener.

8. The catheter section of claim 1 additionally comprising at least one additional ribbon stiffener spirally and coaxially wound upon said inner tubular liner having the same handedness as the first ribbon stiffener.

9. The catheter section of claim 7 additionally comprising at least one additional ribbon stiffener spirally and coaxially wound upon said inner tubular liner having the same handedness as the first ribbon stiffener.

10. The catheter section of claim 7 additionally comprising at least one additional ribbon stiffener spirally and coaxially wound upon said first ribbon stiffener and having the same handedness as the second ribbon stiffener.

11. The catheter section of claim 10 additionally comprising at least one additional ribbon stiffener spirally and coaxially wound upon said first ribbon stiffener and having the same handedness as the second ribbon stiffener.

12. The catheter section of claim 1 where the elongate tubular member has at least one region of variable stiffness between the proximal end and the distal end.

13. The catheter section of claim 11 where the elongate tubular member has at least one region of variable stiffness between the proximal end and the distal end.

14. The catheter section of claim 1 where the first ribbon stiffener has a pitch which varies between the proximal end and distal end.

15. The catheter section of claim 9 where the first ribbon stiffener has a pitch which varies between the proximal end and distal end.

16. The catheter section of claim 7 where the second ribbon stiffener has a pitch which varies between the proximal end and distal end.

17. The catheter section of claim 8 where the second ribbon stiffener has a pitch which varies between the proximal end and distal end.

18. The catheter section of claim 1 where the cover materials are selected from polyimide, polyamides, polyethylene, polypropylene, polyvinylchloride, fluoropolymers including PTFE, FEP, vinylidene fluoride, and their mixtures, alloys, copolymers, and block copolymers, polysulfones or the like.

19. The catheter section of claim 1 where the liner and cover materials are selected from polyurethane, low density polyethylene (LDPE), polyvinylchloride, fluoropolymers including PTFE, FEP, vinylidene fluoride, and their mixtures, alloys, copolymers, and block copolymers.

20. The catheter section of claim 1 where the first ribbon stiffener comprises a ribbon having a thickness between 0.75 mil and 2.5 mil and a width between 2.5 and 8.0 mil.

21. The catheter section of claim 7 where the second ribbon stiffener comprises a ribbon having a thickness between 0.75 mil and 2.5 mils and a width between 2.5 and 8.0 mils.

22. The catheter of claim 1 where at least one of the liner and cover materials are radiopaque.

23. A catheter comprising:
an elongate tubular member having a proximal end and a distal end and a passageway defining an inner lumen extending between those ends,
said elongate tubular member having:
a.) a relatively stiff proximal segment, and
b.) a relatively flexible distal segment, said distal segment being composed of an inner distal tubular liner comprising a distal liner material in coaxial relationship with an outer distal tubular cover comprising a distal cover material, and at least a first ribbon stiffener having a first handedness and spirally and coaxially wound upon said inner distal tubular liner and covered by said outer distal tubular cover, and the catheter, in the region of the distal end, has a critical bend diameter of no more than 3.5 mm and a lateral flexibility of greater than 6500°/in-lb.

24. The catheter of claim 23 wherein the distal section has a lateral flexibility of greater than 8500°/in-lb.

25. The catheter of claim 23 wherein the where the liner material and cover material are miscible in melt form.

26. The catheter of claim 23 where the proximal segment is composed of an inner proximal tubular liner comprising a proximal liner material in coaxial relationship with an outer proximal tubular cover comprising a proximal cover material, and said first ribbon stiffener spirally and coaxially wound upon said inner proximal tubular liner and covered by said outer proximal tubular cover.

27. The catheter of claim 26 further comprising at least one intermediate segment defining a passageway between the relatively stiff proximal segment and the relatively flexible distal segment, said at least one intermediate segment being composed of an extension of the inner proximal tubular liner in coaxial relationship with an extension of the outer distal tubular cover, and said first ribbon stiffener spirally and coaxially wound around said inner proximal tubular liner and covered by said outer distal tubular cover.

28. The catheter of claim 26 where the distal liner material is admixed with the distal cover material in the coaxial region of the first ribbon stiffener.

29. The catheter of claim 28 which is binderless between the distal inner tubular liner and the distal outer tubular cover.

30. The catheter of claim 23 where the proximal and distal liner materials and proximal and distal cover materials are radiation sterilizable without substantial degradation of their physical attributes.

31. The catheter of claim 23 where the catheter additionally comprises a second ribbon stiffener of opposite handedness to the first ribbon stiffener and is spirally and coaxially wound about said first ribbon stiffener.

32. The catheter of claim 23 where at least one of the distal, intermediate, and proximal segments are of constant stiffness.

33. The catheter of claim 27 where at least one of the distal, intermediate, and proximal segments are of constant stiffness.

34. The catheter of claim 27 where at least one of the distal, intermediate, and proximal segments are of variable stiffness.

35. The catheter of claim 31 where at least one of the distal, intermediate, and proximal segments are of variable stiffness.

36. The catheter section of claim 23 where the cover materials are selected from polyimide, polyamides, polyethylene, polypropylene, polyvinylchloride, fluoropolymers including PTFE, FEP, vinylidene fluoride, and their mixtures, alloys, copolymers, and block copolymers, polysulfones or the like.

37. The catheter section of claim 23 where the liner and cover materials are selected from polyurethane, low density polyethylene (LDPE), polyvinylchloride, fluoropolymers including PTFE, FEP, vinylidene fluoride, and their mixtures, alloys, copolymers, and block copolymers.

38. The catheter of claim 23 where the first ribbon stiffener comprises a ribbon having a thickness between 0.75 mil and 2.5 mil and a width between 2.5 and 8.0 mil.

39. The catheter of claim 31 where the second ribbon stiffener comprises a ribbon having a thickness between 0.75 mil and 2.5 mil and a width between 2.5 and 8.0 mil.

40. The catheter of claim 23 where at least one of the liner and cover materials are radiopaque.

41. A catheter comprising:
an elongate tubular member having a proximal end and a distal end and a passageway defining an inner lumen extending between those ends,
said elongate tubular member having:
a.) a relatively stiff proximal segment, said proximal segment composed of an inner proximal tubular liner comprising a proximal liner material in coaxial relationship with an outer proximal tubular cover comprising a proximal cover material, a first ribbon stiffener having a handedness and spirally and coaxially wound upon said inner proximal tubular liner covered by said outer proximal tubular cover and
b.) a relatively flexible distal segment, said distal segment being composed of an inner distal tubular liner comprising a distal liner material in coaxial relationship with an outer distal tubular cover comprising a distal cover material, and said first ribbon stiffener spirally and coaxially wound upon said inner distal tubular liner and covered by said outer distal tubular cover, and the catheter, in the region of the distal end, has a critical bend diameter of no more than 3.5 mm and a lateral flexibility of greater than 6500°/in-lb. and the second ribbon stiffener is spirally and coaxially wound about said first ribbon stiffener, and c.) at least one intermediate segment defining a passageway between the relatively stiff proximal segment and the relatively flexible distal segment, said at least one intermediate segment being composed of an extension of the inner proximal tubular liner in coaxial relationship with an extension of the outer distal tubular cover, and said first ribbon stiffener spirally and coaxially wound between said inner proximal tubular liner and said outer distal tubular cover and the second ribbon stiffener is spirally and coaxially wound about said first ribbon stiffener.

42. The catheter of claim 41 where the first ribbon stiffener comprises a metallic ribbon having a thickness between 0.75 mil and 2.5 mil and a width between 2.5 and 8.0 mil.

43. The catheter of claim 42 where the first ribbon stiffener comprises a ribbon having a thickness of about 1.0 mil and a width of about 3.0 mil.

44. The catheter of claim 42 where the second ribbon stiffener comprises a metallic ribbon having a thickness between 0.75 mil and 2.5 mil and a width between 2.5 and 8.0 mil.

45. The catheter of claim 44 where the first ribbon stiffener comprises a ribbon having a thickness of about 1.0 mil and a width of about 3.0 mil.

46. A catheter section comprising:

an elongate tubular member having a proximal end and a distal end and a passageway defining an inner lumen extending between those ends, said elongate tubular member comprising an outer tubular liner in coaxial relationship with at least a first ribbon stiffener having a handedness and spirally and coaxially wound and covered by said outer tubular cover, and the catheter section, in the region of the distal end, has a critical bend diameter of no more than 3.5 mm and a lateral flexibility of greater than 6500°/in-lb.

47. The catheter section of claim 46 wherein the section has a lateral flexibility of greater than 8500°/in-lb.

48. The catheter section of claim 46 where the cover material is radiation sterilizable without substantial degradation of its physical attributes.

49. The catheter section of claim 46 where the catheter section additionally comprises a second ribbon stiffener of opposite handedness to the first ribbon stiffener spirally and coaxially wound upon said first ribbon stiffener.

50. The catheter section of claim 46 additionally comprising at least one additional ribbon stiffener having the same handedness as the first ribbon stiffener.

51. The catheter section of claim 46 where the elongate tubular member has at least one region of variable stiffness between the proximal end and the distal end.

52. The catheter section of claim 46 where the first ribbon stiffener has a pitch which varies between the proximal end and distal end.

53. The catheter section of claim 49 where the second ribbon stiffener has a pitch which varies between the proximal end and distal end.

54. The catheter section of claim 46 where the cover materials are selected from polyimide, polyamides, polyethylene, polypropylene, polyvinylchloride, fluoropolymers including PTFE, FEP, vinylidene fluoride, and their mixtures, alloys, copolymers, and block copolymers, polysulfones or the like.

55. The catheter section of claim 46 where the first ribbon stiffener comprises a ribbon having a thickness between 0.75 mil and 2.5 mil and a width between 2.5 and 8.0 mil.

* * * * *

UNITED STATES PATENT AND TRADEMARK OFFICE
CERTIFICATE OF CORRECTION

PATENT NO. : 5,454,795
DATED : October 3, 1995
INVENTOR(S) : SAMSON

It is certified that error appears in the above-indentified patent and that said Letters Patent is hereby corrected as shown below:

Column 3, line 66, insert --be-- after "may".

Column 8, line 31, change "Of" to --of--.

Column 10, line 10, insert --been-- prior to "portrayed".

Claim 3, column 10, line 33, delete "wherein the".

Signed and Sealed this

Thirteenth Day of May, 1997

BRUCE LEHMAN

Attest:

Attesting Officer

Commissioner of Patents and Trademarks